United States Patent [19]  [11] Patent Number: 4,661,611
Narang et al. [45] Date of Patent: Apr. 28, 1987

[54] POLYFUNCTIONAL ACYLSILANE CROSSLINKING AGENTS AND PHOTOCROSSLINKING SYSTEMS COMPRISING THE SAME

[75] Inventors: Subhash C. Narang, Menlo Park, Calif.; Richard Vicari, Astoria; Juesheng Gu, Brooklyn, both of N.Y.

[73] Assignee: Fuji Photo Film Co., Ltd., Kanagawa, Japan

[21] Appl. No.: 805,537

[22] Filed: Dec. 6, 1985

[51] Int. Cl.⁴ ............................................... C07F 7/08
[52] U.S. Cl. ................................... 556/418; 525/342; 522/130; 556/436
[58] Field of Search ................. 526/279; 525/342; 522/130; 556/418, 436

[56] References Cited

U.S. PATENT DOCUMENTS 4,094,756  6/1978  Taylor .................................. 522/130

Primary Examiner—Paul R. Michl
Attorney, Agent, or Firm—Sughrue, Mion, Zinn, Macpeak & Seas

[57] ABSTRACT

Polyfunctional acyl silanes of the formula

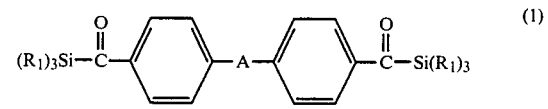

are disclosed as novel crosslinking agents. Composition and processes involving the same are also disclosed.

7 Claims, No Drawings

POLYFUNCTIONAL ACYLSILANE CROSSLINKING AGENTS AND PHOTOCROSSLINKING SYSTEMS COMPRISING THE SAME

BACKGROUND OF THE INVENTION

1. Field of the Invention

The present invention relates to novel polyfunctional acyl silane photocrosslinking agents, photocrosslinkable compositions comprising the same and a photocrosslinking process using the same.

2. Description of the Prior Art

We are aware of no prior art which discloses the polyfunctional acyl silanes of the present invention or suggests the use of the same in photocrosslinking compositions.

The closest prior art of which we are aware is represented by U.S. Pat. No. 2,940,853 Sagura et al which discloses bis-azides as photocrosslinking agents for the photocrosslinking of polymers.

U.S. Pat. No. 3,758,306 Roos discloses photopolymerizable compositions and elements containing organosilanes.

U.S. Pat. No. 3,924,520 Boardman et al deals with preparing lithographic plates utilizing vinyl monomers containing hydrolyzable silane groups.

U.S. Pat. No. 3,953,212 Miyano discloses a presensitized lithoprinting plate comprising a support and a coating layer of a mixture of a photosensitive material and a silicone rubber.

U.S. Pat. No. 4,245,056 Bock et al discloses crosslinking high density polyethylenes with t-octyl silicon peroxides.

SUMMARY OF THE INVENTION

The present invention provides novel polyfunctional acyl silanes which are particularly effective as high sensitivity photocrosslinking agents for the photocrosslinking of polymers.

The present invention further provides photocrosslinkable polymer systems and methods of photocrosslinking such polymer systems.

The major object of the present invention is to provide novel photocrosslinking agents, polymer systems comprising the same and processes of photocrosslinking using the same.

DESCRIPTION OF THE PREFERRED EMBODIMENTS

The novel polyfunctional acyl silanes of the present invention are bifunctional, trifunctional or tetrafunctional acyl silanes. Bifunctional acyl silanes are preferred.

Accordingly, they have more than one acyl silane moiety per molecule.

They can be represented by the following formula:

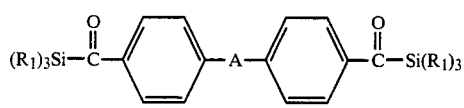

In the above formula, A can be —O—R—O or —NH—R—NH—; moiety A links the two substituted phenyl moieties.

In moiety A, R can be —(CH$_2$)$_n$—, where n is 1–12, preferably 1–10 and most preferably 1–6, or

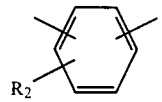

where R$_2$ can be hydrogen, alkyl, halogen, alkoxy or the group

where R$_3$ and R$_4$ can be C$_1$ to C$_6$ alkyl or hydrogen, with the proviso that R$_3$ and R$_4$ are not simultaneously hydrogen.

Preferred alkyl groups for R$_2$ include C$_1$ to C$_6$ alkyl groups; preferred halogen atoms for R$_2$ are chlorine, fluorine, bromine and iodine and preferred alkoxy groups for R$_2$ include C$_1$ to C$_6$ alkoxy groups.

It is most preferred that when group R comprises the phenyl moiety substituted with R$_2$ that the linkages to the —O— atoms or the —NH— groups be para each other, with meta providing intermediate results and ortho providing worse results.

The

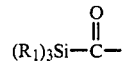

groups on each phenyl moiety may be the same or different. It is preferred that they be the same. They may be substituted ortho, meta or para the position that the phenyl group is bonded to the A group. It is most preferred that substitution be para, with meta substitution providing intermediate effects and ortho substitution providing worse effects from the viewpoint of steric and electronic effects and sensitivity to irradiation. Para substitution is far superior to meta or ortho substitution.

R$_2$ can be electron donating or electron withdrawing; the exact nature of R$_2$ is not overly important.

If the polyfunctional acyl silanes of the present invention are bifunctional, they have the capability to photocrosslink two polymer chains; if trifunctional they have the capability to photocrosslink three polymer chains and if tetrafunctional they have the capability to photocrosslink four polymer chains.

R$_1$ is an unsubstituted alkyl group or an aryl group. Preferably, R$_1$ is an alkyl group with 1 to 6 carbon atoms or a phenyl or naphthyl group. Most preferably, R$_1$ is methyl. Preferred groups include, using the abbreviations Me to represent methyl, t-Bu to represent tertiary butyl and Ph to represent phenyl, Me$_3$Si, t-BuMe$_2$Si, Ph$_3$Si and t-BuPh$_2$Si.

The currently most preferred polyfunctional acyl silane is the following bis-acylsilane:

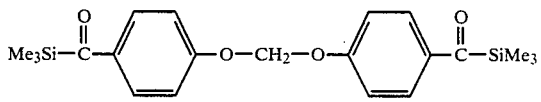

The main reason for preference is the excellent compatibility thereof with the polymer matrix, e.g., a hydroxyethylmethacrylate/n-butyl methacrylate copolymer matrix (HEMA/butyl methacrylate copolymer). Other acylsilanes with longer spacer groups, e.g., $(CH_2)_6$ instead of $CH_2$, did not provide films of a quality as good as the above bis-acylsilane.

Homopolymers, copolymers and graft copolymers can be crosslinked using the novel polyfunctional acyl silanes of the present invention. The nature of the polymer photocrosslinked is not overly important so long as the polymer has OH and/or $NH_2$ groups. Illustrative polymers include polymers formed from vinyl alcohol, hydroxy styrene, acrylic acid, methacrylic acid, hydroxyalkyl acrylates, hydroxyalkyl methacrylates, acrylamides and vinylamines. These materials can, of course, be substituted. For example, a typical substituted monomer would include poly-α-alkyl acrylic acid. Preferably any alkyl group will have from 1 to 6 carbon atoms.

The nature of the comonomer or graft comonomer is not overly important; the comonomer containing the reactive functionality OH and/or $NH_2$ should, however, comprise at least about 10 mole % of any copolymer or graft copolymer. Mixtures of homopolymers, copolymers and/or graft copolymers can, of course, be used.

Obviously in a homopolymer every recurring unit will have the required OH and/or $NH_2$ reactive functionality. This will not generally be the case in a copolymer or graft copolymer, though this could be the situation where both comonomers contain the reactive OH and/or $NH_2$ functionality; in the case of a copolymer or graft copolymer it is preferred that at least one out of every four comonomer units have the OH and/or $NH_2$ reactive functionality, and it is most preferred that at least one out of every three comonomer units have the reactive functionality OH and/or $NH_2$.

Since we generally prefer to achieve the maximum reaction possible (maximum crosslinking), usually the greater the amount of monomer units which contain the OH and/or $NH_2$ groups, the better. For instance, in the later presented Example where a HEMA/butylmethacrylate copolymer is used, the copolymer comprises 81.4% HEMA/18.6% n-butylmethacrylate monomer units. In fact, based on results to date we have not found any comonomers or graft comonomers that are not useful so long as the final copolymer or graft copolymer comprises at least about 10 mole % of the comonomer containing the reactive functionality OH and/or $NH_2$. When a graft copolymer is formed with a backbone which does not contain the reactive functionality OH and/or $NH_2$, the comonomer containing the reactive functionality OH and/or $NH_2$ is grafted onto the parent polymer. Techniques of forming such copolymers or graft copolymers are well known in the art and will not be recited herein. We expect the polyalkenes and polyalkene oxides to be most useful in forming graft copolymers, for example, materials such as polyethylene and polypropylene oxide should provide excellent results. More than two comonomers may, of course, be used in forming a copolymer or a graft copolymer.

For best results, it is preferred that any polymer photocrosslinked using the novel polyfunctional acyl silanes of the present invention have a high molecular weight (molecular weights herein are weight average unless otherwise indicated), most preferably at least about 20,000 up to about 100,000. Polymers of a molecular weight greater than about 100,000 can be used so long as films can be cast therefrom. As molecular weight increases, sensitivity increases, and this is the major reason that we prefer to use higher molecular weight materials.

It is to be noted that we prefer that the reactive functionality OH and/or $NH_2$ be farther removed from the polymer backbone to which it is attached rather than being directly attached. For example, with HEMA, where the reactive functionality OH is separated from the chain to which it is attached, we achieve greater sensitivity then with polyvinyl alcohol. As can be seen from the listing of earlier illustrated polymers which containing the reactive functionality OH and/or $NH_2$, we most prefer to use vinyl polymers with a relatively low number of carbon atoms as the comonomer containing the reactive functionality OH and/or $NH_2$.

Useful solvent(s) for film casting and for image development include ethers such as THF, dioxane, lower alcohols such as ethanol, isopropanol, propanol, butanol, etc., ketones such as acetone, methylethyl ketone, methylisobutyl ketone, cyclohexanone, etc., esters such as ethyl acetate, Cellosolve, etc., amides such as dimethyl formamide, dimethyl acetamide, etc., halogenated hydrocarbons such as dichloromethane, chloroform, chlorobenzene, etc.

We usually use a mixture of solvents, typically a mixture of a relatively good solvent for the system in combination with a relatively poor solvent for the system. The criteria that we use in selecting any particular solvent mixture or any particular solvent is to insure that all components are soluble in the solvent(s), the solvent does not evaporate too fast for ease of use, the resulting system shows a viscosity adapted to the procedures selected for applying the system, typically spinning, and the system exhibits good film forming properties.

The polyfunctional acyl silanes of the present invention can be used to photocrosslink polymers containing the reactive OH or $NH_2$ moiety, or both of such moieties, upon exposure to radiation. Preferably the radiation is ultraviolet radiation, but we believe that electron beams, X-rays and gamma-rays can also be used with equal success.

Crosslinking is best achieved at an intensity of about 10 to about 100 millijoules/$cm^2$, though this is not limitative, and we expect that sensitivity significantly lower than 10 mJ/$cm^2$ are achievable.

The novel photocrosslinkable systems of the present invention can be used in any environment where photocrosslinkable polymers have been used in the past. They find particular application in the manufacture of integrated circuits as a negative photoresist.

In use, the polymer, a convenient solvent and the novel polyfunctional acyl silane photocrosslinking agent(s) of the present invention are mixed, most conveniently with a trace of pyridine to stabilize the final photocrosslinked product. Usually a trace amount up to about 2 wt % of a stabilizer, such as pyridine, based on the weight of solvent is used.

While the use of a sensitizer is optional, it substantially increases sensitivity. To date, Michler's ketone has provided the best results.

The polyfunctional acyl silanes of the present invention show a tendency to crystallize out of films; accordingly, we prefer to use from about 5 to about 25 wt %, more preferably from about 10 to about 15 wt % of the polyfunctional acyl silane or polyfunctional acyl silanes, based on the weight of the total formulation after solvent drive-off (hereafter all percentages are weight percentages based on the weight of the total formulation after solvent drive-off unless otherwise indicated).

When a sensitizer is used, and for practical purposes a sensitizer will generally be used to increase sensitivity, normally it is used in an amount of about 10 wt % to about 20 wt % of the total formulation. If too much sensitizer is used, as will be appreciated by one skilled in the art, film properties are deteriorated. For example, we obtain better results when the amount of sensitizer is reduced to 10 wt % and the amount of polyfunctional acyl silane was increased to 20 wt % as opposed to the situation where the amount of sensitizer used was 20 wt % and the amount of polyfunctional acyl silane was 10 wt %.

The reason that a stabilizer should be present in the final product of the present invention is that the photo-crosslinked film produced in accordance with the present invention, due to the presence of the polyfunctional acyl silane, will tend to hydrolyze unless a tertiary amine is present. Based on results to date, aliphatic and aromatic tertiary amines in general are useful. The amount of amine is not overly important so long as a trace amount is present. In addition to pyridine, other commonly available tertiary amines useful to perform a stabilizing function in accordance with the present invention include quinoline and triethylamine. Other tertiary amines may, of course, be used.

Following application of the system, typically by spinning, though any means can be used, the system is then pre-baked at, e.g., 80° C. under vacuum for about 30 minutes to out gas solvent.

The system is merely applied to yield a dry resist layer of a thickness as is conventional in the art and which can vary substantially depending on the use. This will be apparent to one skilled in the art.

The system is then ready for exposure and photo-crosslinking, normally using ultraviolet radiation at levels as earlier described.

The exposed photocrosslinked system can then be developed in any convenient solvent, for example, ethanol (1 volume part):acetone (5 volume parts) for 1 to 2 minutes at room temperature.

Normally a post-bake is then conducted to remove residual solvent, for example, at 80° C. for an appropriate time. We have found that 1 hour is more than adequate to dry residual solvent off.

After use, if desired, the photocrosslinked material can then be stripped with pure tetrahydrofuran, pure ethanol, etc.

By choosing an appropriate solvent(s) for film casting and for image development as earlier exemplified, we have increased the sensitivity to 11 mJ/cm$^2$. This sensitivity is very high for negative resist formulations that are resistant to oxygen plasma etching. This is the only negative resist we know, (sensitive to mid UV) which contains silicon in the crosslinking agent. Therefore, it is recommended that the amount of polyfunctional acyl silane used should be higher than is the case with conventional bis-azides, so that the resulting imaged layer has enough silicon content to be resistant to oxygen plasma etching if this is desired or necessary. This is not done with bis-azide resists.

Our results to date establish that the polyfunctional acyl silanes of the present invention are:

Useful in applications in general where conventional bis-azide-based resists are used in a manner substantially identical to bis-azide based resists; and Have built-in resistance to oxygen plasma etching, a capability not illustrated in bis-azide resists; and A typical synthesis procedure per the present invention is schematically illustrated below and then explained in detail.

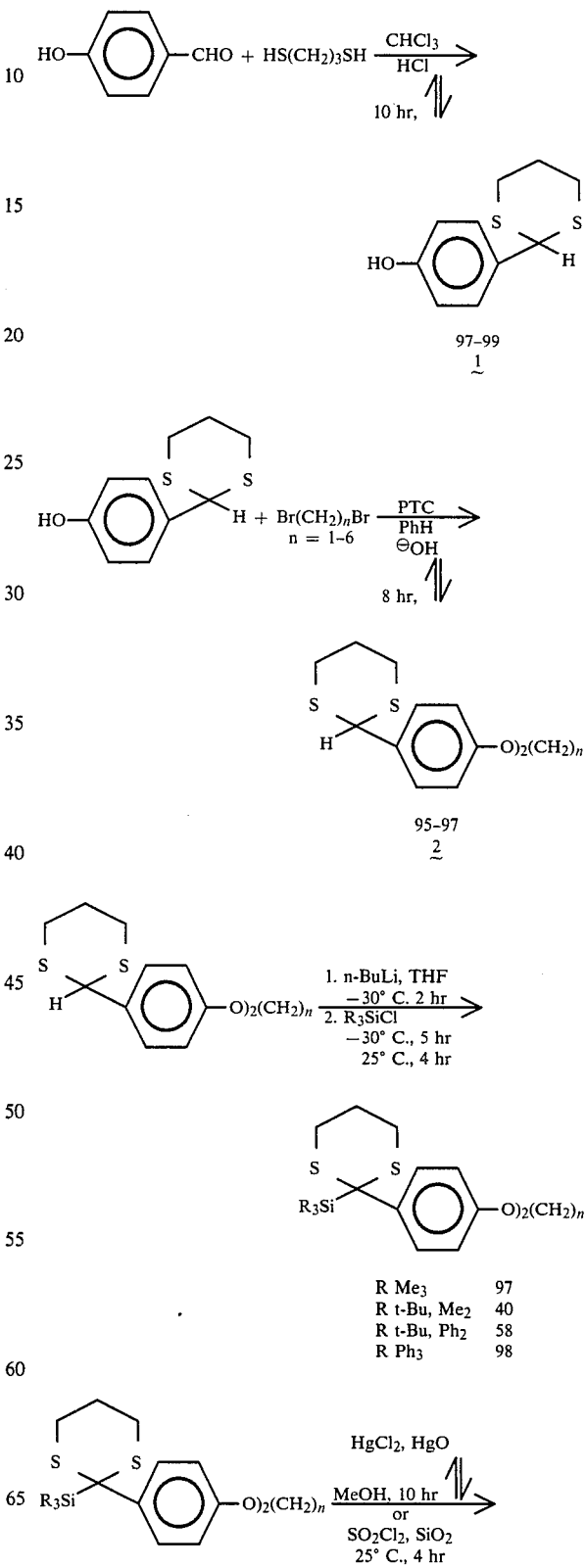

-continued

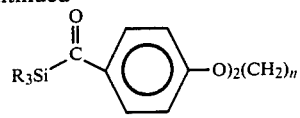

Synthesis of 2-(4-hydroxyphenyl)-1,3-dithiane: (1)

4-Hydroxybenzaldehyde (46 g, 0.377 mol), recrystallized from benzene, and 1,3-propanedithiol (45 ml, 0.449 mol) were added to dry chloroform. The reaction mixture was stirred at 0° C. and HCl gas was bubbled through the solution for 10 minutes. After the exothermic reaction stopped the solution was refluxed for 10 hours. A white precipitate formed. This was filtered off and the chloroform solution was washed with water three times, dried (MgSo4) and evaporated under reduced pressure to yield a light yellow solid. White needles were obtained after recrystallization from chloroform, MP=151°-152° C. The white precipitate was also recrystallized from chloroform to yield white needles that melted at 151°-152° C. IR and NMR confirmed the two compounds to be identical. Total yield after recrystallization: 99%.

NMR(CDCl) 7.26(d), 6.86(d), 5.22(s), 2.86(m) and 2.01(m).

IR(KBr) 3300 cm$^{-1}$ (OH), 910 cm$^{-1}$ (dithiane ring). The aldehyde peaks at 2700 cm$^{-1}$ and 2800 cm$^{-1}$ and the carbonyl peak at 2670 cm$^{-1}$ disappeared.

Synthesis of bis(2-(4-phenoxy)-1,3-dithiane) methane: (2)

1 (10 g, 47 mmol) was dissolved in NaOH(aq) with tetrabutyl ammonium hydrogen sulfate (2 g). Dibromomethane (4.1 g, 24 mmol), dissolved in benzene, was added and the two phase solutions mechanically stirred at reflux for 8 hours. The reaction system was cooled to room temperature and the layers separated. The benzene layer was washed with water, 10% KOH, water and dried over MgSO4. Evaporation under reduced pressure yielded a white solid that was flash chromatographed on silica gel using CHCl3 as the eluant. MP=171°-172° C., yield (97.4%).

NMR (CDCl3) 7.35(d), 7.09(d), 5.68(s), 5.11(s), 2.91(m) and 2.07(m).

IR(KBr), the peak at 3300 cm$^{-1}$ disappeared.

General Procedure for the Preparation of 2-Lithio-1,3-dithiane Solutions in THF

A dry three-neck flask fitted with a reflux condenser, two addition funnels and a magnetic stir bar is flushed with dry argon. The addition funnels are sealed with septa and the condenser is fitted with an argon balloon. The dithiane (1 mol) in dry THF is added by syringe into one of the addition funnels. The flask is cooled down to −30° C. and the dithiane solution added to the flask. The funnel is rinsed with THF to insure complete transfer. n-BuLi (1.6M in hexane, 2 mol) is then added dropwise via the other addition funnel. A dark red color appeared after the addition. The solution was stirred at −30° C. for 2 hours.

Silylation of the 2-Lithio-1,3-dithiane Solutions in THF

A typical silylation procedure is as follows:

Freshly distilled chlorosilane (2 mol) is added dropwise at −30° C. The dark red color immediately turns clear after the addition. The reaction solution is allowed to reach room temperature whereupon a white precipitate formed (LiCl) and stirring is continued for 4 hours. The reaction is carefully quenched with water. The bulk of the solvent is removed under reduced pressure and the residue taken up in CH2Cl2. The CH2Cl2 is washed with water, 10% KOH, water, dried over Na2SO4 and evaporated under reduced pressure to yield a pale yellow solid. Recrystallization from CH2Cl2 yielded a white solid.

NMR (CDCl3) 7.78(d), 7.18(d), 5.76(s), 2.48(m), 1.97(m) and 0.1(s).

IR(KBr) peaks at 1240 cm$^{-1}$ and 840 cm$^{-1}$ correspond to the trimethylsilyl group.

General Procedure for the Hydrolysis of 2-Silyl-1,3-dithiane Derivatives

Mercuric Chloride Method

A solution of the silyl dithiane in aqueous 90% methanol is added at 25° C. to a stirring solution of mercuric chloride (4.4 mol) in the same solvent mixture (25 ml). Mercuric oxide (2.2 mol) is added to buffer the reaction mixture. The dithianemercuric chloride complex separated as a flocculent white precipitate. The mixture is stirred and refluxed under argon for 8-10 hours. The mixture is cooled and filtered. The filter cake is washed with chloroform and the organic phase is washed with water, ammonium acetate, water and brine and dried over sodium sulfate. Evaporation of the solvent yielded a yellow gummy solid which upon flash chromatography gave a yellow solid.

Sulfuryl Chloride Method

When the substituent(s) on the silicon were aromatic, this method gave the best results. A solution of sulfuryl chloride (2.4 mol) in dichloromethane is added dropwise at room temperature to a stirring solution of the silyl dithiane (1 mol) and wet silica gel (0.5 g) in dichloromethane. After stirring for 4-5 hours at room temperature, powdered potassium carbonate is added to the reaction mixture and stirring is continued for 30 minutes. Filtration and evaporation under reduced pressure yields a yellow gummy solid which gave a yellow solid after flash chromatography.

Other polyfunctional acyl silanes can be formed in an anologous matter by changing the starting materials in a manner which will be obvious to one skilled in the art.

Having thus generally described the invention, the following Example is presented.

EXAMPLE

Four photocrosslinkable compositions were formed by well mixing the components set forth in the following Table. There was no criticality to the mixing procedure, rather, all components were merely dissolved in the DMF.

The system was then spin coated in a conventional manner onto a transparent substrate to a conventional thickness as is commonly used for electronic circuit manufacture.

Following spin casting, the system was prebaked at 80° C. for 30 minutes under vacuum to remove solvent.

Each of the four systems was then image-wise exposed using mid-UV at 410 nm and an intensity as shown by the Sensitivity Figure given in mJ/cm$^2$ in the Table.

The resulting crosslinked photoresists were then developed in an ethanol-acetone mixture (1:5 v/v) at room temperature for 1 to 2 minutes. In each instance, the crosslinked photoresist, which was a negative photoresist, was cleanly removed in the unexposed areas yet remained adherent to the substrate in desired areas.

TABLE

|  | Composition (pphr) | | | |
| --- | --- | --- | --- | --- |
| Bis (Acylsilane) | 26.8 | 26.8 | 13.4 | 13.4 |
| Michler's ketone | 13.4 | 26.8 | 13.4 | 0 |
| HEMA/butylmethacrylate copolymer (M.W. ca. 30,000) | 100 | 100 | 100 | 100 |
| Pyridine | 67 | 67 | 67 | 67 |
| DMF | 15240 | 15240 | 15240 | 15240 |
| Sensitivity (mJ/cm$^2$) | 11 | 27 | 60 | 1000 |

It is expected that the use of higher molecular weight polymers and trifunctional (or tetrafunctional) acylsilanes will result in even significantly higher sensitivity.

While there have been described what are at present considered to be the preferred embodiments of this invention, it will be obvious to those skilled in the art that various changes and modifications can be made therein without departing from the invention, and it is, therefore, intended to cover all such changes and modifications as fall within the true spirit and scope of the invention.

What is claimed is:

1. Polyfunctional acyl silanes having the formula:

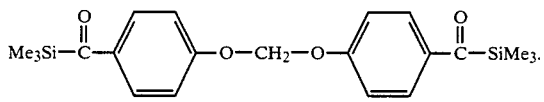

where A is —O—R—O— or —NH—R—NH—, R is —(CH$_2$)$_n$— where n is 1 to 12 or

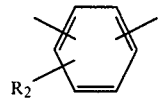

where R$_2$ is hydrogen, alkyl, halogen, alkoxy or the group

where R$_3$ and R$_4$ are C$_1$ to C$_6$ alkyl or hydrogen, with the proviso that R$_3$ and R$_4$ are not simultaneously hydrogen, and wherein R$_1$ is an unsubstituted alkyl group or an aryl group.

2. The polyfunctional acyl silanes as claimed in claim 1, wherein R$_2$ is hydrogen, a C$_1$ to C$_6$ alkyl group, chlorine, fluorine, bromine or iodine or a C$_1$ to C$_6$ alkoxy group.

3. The polyfunctional acyl silanes as claimed in claim 1, which are bifunctional.

4. Polyfunctional acyl silanes as claimed in claim 1, wherein both (R$_1$)$_3$Si groups are the same.

5. Polyfunctional acyl silanes as claimed in claim 1, wherein the

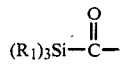

groups are both substituted para to the A group.

6. Polyfunctional acyl silanes as claimed in claim 1, wherein both R$_1$ groups are the same and are methyl.

7. Polyfunctional acyl silanes as claimed in claim 1, wherein the acyl silane is the material

* * * * *